US005681862A

United States Patent [19]

Hollis et al.

[11] Patent Number: 5,681,862

[45] **Date of Patent: *Oct. 28, 1997**

[54] IONENE POLYMERS AS MICROBICIDES

[75] Inventors: C. George Hollis, Germantown; Percy A. Jaquess, Tigrett, both of Tenn.

[73] Assignee: Buckman Laboratories International, Inc., Memphis, Tenn.

[ * ] Notice: The term of this patent shall not extend beyond the expiration date of Pat. No. 5,051,124.

[21] Appl. No.: 27,097

[22] Filed: Mar. 5, 1993

[51] Int. Cl.[6] .......................... A01N 33/12; C07C 211/62

[52] U.S. Cl. .......................... 514/642; 514/837; 514/292

[58] Field of Search .......................... 514/837, 642; 564/292

[56] References Cited

U.S. PATENT DOCUMENTS

| | | | |
|---|---|---|---|
| Re. 28,808 | 5/1976 | Panzer et al. | 260/2 BP |
| 3,738,945 | 6/1973 | Panzer et al. | 260/2 BP |
| 3,778,476 | 12/1973 | Rembaum et al. | 260/567.6 P |
| 3,874,870 | 4/1975 | Green et al. | 71/67 |
| 3,894,946 | 7/1975 | Panzer et al. | 210/54 |
| 3,894,947 | 7/1975 | Panzer et al. | 210/54 |
| 3,898,336 | 8/1975 | Rembaum et al. | 260/567.6 P |
| 3,930,877 | 1/1976 | Aitken | 106/287 R |
| 3,931,319 | 1/1976 | Green et al. | 260/567.6 T |
| 4,025,627 | 5/1977 | Green et al. | 424/248.4 |
| 4,027,020 | 5/1977 | Green et al. | 424/248.56 |
| 4,054,542 | 10/1977 | Buckman et al. | 260/26 P |
| 4,089,977 | 5/1978 | Green et al. | 424/329 |
| 4,104,161 | 8/1978 | Wein | 210/54 |
| 4,111,679 | 9/1978 | Shair et al. | 71/67 |
| 4,147,627 | 4/1979 | Goodman | 210/58 |
| 4,164,521 | 8/1979 | Goodman | 528/187 |
| 4,166,041 | 8/1979 | Goodman | 252/180 |
| 4,325,940 | 4/1982 | Green et al. | 564/292 |
| 4,506,081 | 3/1985 | Fenyes et al. | 548/523 |
| 4,581,058 | 4/1986 | Fenyes et al. | 71/67 |
| 4,606,773 | 8/1986 | Novak | 106/213 |
| 4,769,155 | 9/1988 | Dwyer | 210/728 |
| 4,778,813 | 10/1988 | Fenyes et al. | 514/357 |
| 4,970,211 | 11/1990 | Fenyes et al. | 514/252 |
| 5,051,124 | 9/1991 | Pera | 71/67 |
| 5,093,078 | 3/1992 | Hollis et al. | 422/16 |
| 5,128,100 | 7/1992 | Hollis et al. | 422/14 |
| 5,162,111 | 11/1992 | Grabstein et al. | 424/85.1 |

FOREIGN PATENT DOCUMENTS

| | | |
|---|---|---|
| 1259971 | 10/1955 | France . |
| 2126579 | 3/1984 | United Kingdom . |

OTHER PUBLICATIONS

Sydney M. Finegold and William J. Martin, "Bailey and Scott's Diagnostic Microbiology," (6th ed., 1982), Contents, xi–xiii.

Noel R. Krieg and John G. Holt, "Bergey's Manual of Systematic Bacteriology," (1984) 1, Contents :xxiii.

Roger Y. Stanier, Edward A. Adelberg, and John Ingraham, "The Microbial World," 4th ed., (New Jersey: Prentice–Hall, Inc.), Contents, vii–xvii.

A. Rembaum, "Biological Activity of Ionene Polymers," Applied Polymer Symposium No. 22, 299–317 (John Wiley & Sons, Inc., 1973).

W.K. Joklik et al., "Zinsser Microbiology," (Appleton & Lange, Connecticut) (1992), Contents, iii–v.

Technical Disclosures for: BUSAN® 77 Rev. Aug. 5, 1992

BUSAN® 79 Rev. Aug. 23, 1991.

BUSAN® 1055 Rev. Dec. 6, 1991.

BUSAN® 1099 Rev. Oct. 4, 1991.

BUSAN® 1157 Rev. Jul. 21, 1991.

Gerba et al., "Removal of Poliovirus and Rotavirus from Tapwater by a Quaternary Ammonium Resin", Chemical Abstracts, vol. 100, No. 20, Abstract No. 161635, May 14, 1984.

S.S. Block, *Disinfection, Sterilization and Preservation*, Lea & Febiger, (1991), Philadelphia, USA, Chapter 13: "Quaternary Ammonium Antimicrobial Compounds" by J. Merianos, pp. 225–255.

S.S. Block, *Disinfection, Sterilization and Preservation*, Lea & Febiger, (1991), Philadelphia, USA, Chapter 45: "Food–And Water–Infective Microorganisms" by J. Lopes, pp. 773–790.

*Primary Examiner*—Peter O'Sullivan

*Attorney, Agent, or Firm*—Armstrong, Westerman, Hattori, McLeland & Naughton

[57] ABSTRACT

A method for controlling the growth of at least one microorganism in an aqueous system susceptible to the growth of said microorganism and in recognized need of said control comprising the step of adding to said aqueous system an ionene polymer in an amount effective to inhibit the growth at least one microorganism selected from *Campylobacter spp., Mycobacterium spp., Shigella spp., ribrio spp., Yersinia spp., Entamoeba spp.,* and poliovirus. The aqueous system is selected from potable water, sewage, and other nonmarine surface water. Methods for controlling the spread of the diseases cholera and polio are also disclosed.

7 Claims, No Drawings

IONENE POLYMERS AS MICROBICIDES

This invention relates to methods for the microbicidal control of microorganisms in aqueous systems by treating the system with an effective amount of an ionene polymer. Particularly, it relates to methods for controlling the growth of species (ssp.) within the bacterial genera Campylobacter, Shigella, Vibrio and Yersinia, and protozoa within the genus Entamoeba in aqueous systems such as potable water, sewage and other nonmarine surface water. This invention also relates to methods for controlling the growth of the bacteria *Mycobacterium boris, Salmonella typhi,* and the fungus *Candida albicans* in these nonmarine aqueous systems. This invention further relates to methods for controlling poliovirus in potable water, sewage, and other nonmarine surface water. Methods for controlling the spread of the diseases cholera and polio are also disclosed.

Cholera is endemic in regions of India and Bangladesh, and has spread to other regions of the globe in a series of pandemics. Recent cholera pandemics from the 1960s through the 1980s have involved Africa, the Philippines, Western Europe and Southeast Asia. In the United States, the number of cases of cholera has increased during the past fifteen years. Zinsser Microbiology 566–73 (W. K. Joklik, H. P. Willett, D. B. Amos, C. A. Wilfert, eds., 20th ed., 1992). Cholera struck recently in Latin America, where the epidemic has affected more than half a million people, resulting in the death of tens of thousands of Latin Americans. The cholera epidemic that currently plagues Latin America began in Peru in 1990, and has spread at least as far as Brazil, Guatemala, Mexico, and Nicaragua. The Pan American Health Organization acknowledged that "once cholera arrives on a continent, it's likely to remain endemic until we make vast improvements in water and sanitation." Christine Tierney, *Central America Suffers Summertime Cholera Surge,* Reuter Newswire, Sep. 4, 1992.

*Vibrio cholerae* is the species of the bacterial genus Vibrio, which causes epidemic cholera, and is among the leading causes of other gastrointestinal infections. *V. parahaemolyticus* is another Vibrio that causes gastrointestinal infection, and is prevalent in the United States. Other *Vibrio ssp.* may cause human illnesses that include diarrhea, bloody diarrhea, vomiting, cramps, sepsis and soft tissue infections. For example, *V. vulnificus* may produce infection in a preexisting wound or ulcer, or may cause primary sepsis that may be accompanied by shock that may be fatal. *V. alginolyticus* may also infect wounds, cause middle ear infections (otitis media), or cause bacteremia. S. M. Finegold, W. J. Martin, *Diagnostic Microbiology* 86–87, 240–46 (6th ed. 1982). Vibrio ssp. also cause disease in fishes, eels, frogs, other vertebrates and invertebrates as well. See 1 *Bergey's Manual of Systematic Bacteriology* 518–38 (N. R. Krieg and J. G. Bolt eds. 1984).

Vibrio bacteria are aquatic bacteria distributed throughout the world which often dangerously contaminate aqueous systems and water supplies. Contaminated water supplies pose the most serious source of Vibrio infection, as Vibrio-associated diseases are transmitted almost exclusively by the fecal contamination of water systems and food materials.

In countries lacking adequate potable water purification facilities, illness is often caused by drinking water contaminated with the bacteria. The drinking of contaminated water is the primary cause of the current cholera pandemics.

In developed countries, Vibrio-associated illness is more often caused by the eating of contaminated seafood or shellfish. The contamination results from releasing inadequately treated sewage into the marine environment.

For example, ingestion of raw oysters contaminated with *V. vulnificus* may lead to septicemia in as little as twenty-four hours. Thus, the major defense in the control of Vibrio-associated illness is the maintenance of adequate water purification and adequate sewage treatment systems. R. Y. Startler, E. A. Adelberg, J. L. Ingraham, *The Microbial World* 627–29 (1976).

In addition to Vibrio bacteria, the methods of control disclosed herein can be used to control the growth of other microorganisms known to possess the potential to cause waterborne diseases. Members of the genus Campylobacter are bacteria pathogenic for humans and other meals. Campylobacter is a major cause of diarrhea in adults and children, causing diarrhea as frequently as do Salmonella and Shigella.

Fever, thrombophlebitis, bacteremia, septic or reactive arthritis, endocarditis, meningoencephalitis, pericarditis, pleuropulminary infection, cholecystitis, diarrhea and septic abortion may be causedby *C. fetus* subspecies (ss.) jejuni, or *C. fetus ss. intestinalis infection.* Contaminated water is an important vehicle of infection. S. M. Finegold, W. J. Martin, *Diagnostic Microbiology* 280–81 (6th ed. 1982).

Enteropathogenic Escherichia coli are responsible for outbreaks of diarrhea in infants and newborns, and diarrhea, including "traveler's diarrhea", in adults. *E. coli* may be invasive and toxin-producing, causing sometimes fatal infections, such as cystitis, pyelitis, pyelonephritis, appendicitis, peritonitis, gallbladder infection, septicemia, meningitis and endocarditis. Finegold & Martin, at 84–85, 222.

*Mycobacterium boris,* like *M. tuberculosis, M. africanum, M. ulcerans,* and *M. leprae,* is a strict patbogen. *M. bovis* is a significant patbogen throughout much of the world, causing tuberculosis, primarily in cattle. Finegold & Martin, at 351–52.

Opportunistic in nature, *Pseudomonas aeruginosa* may infect burn or wound sites, or the urinary or lower respiratory tracts of immunocompromised hosts. Infection may result in serious septicemia. Finegold & Martin, at 249, 253.

*Salmonella spp.* cause food poisoning, resulting in nausea, vomiting, diarrhea and sometimes-fatal septicemia. *S. typhi* is the etiological agent of typhoid fever. Finegold & Martin, at 204–06.

*Shigella spp.,* including *S. dysenteriae,* are common waterborne pathogenic agents, causing bacillary dysentery as well as bacteremia and pneumonia. In the United States and Canada, *S. sonnei* and *S. flexneri* have become the most common etiological agents in bacillary dysentery. Finegold & Martin, at 219–221.

*Staphylococcus aureus* causes one of the most common types of food poisoning. Additionally, various skin infections and more serious diseases, such as toxic shock syndrome, septicemia, meningitis and pneumonia may result from S. aureus infection. Finegold & Martin, at 165–66.

Bacteria of the genus Yersinia are also pathogens. *Y. enterocolitica* is an enteric patbogen. Infection with this microorganism causes severe diarrhea, gastroenteritis and other types of infections such as bacteremia, peritonitis, cholecystis, visceral abscesses, and mesenteric lymphadenitis. Septicemia with 50% mortality has been reported. *Y. pestis* is the etiologic agent of bubonic, pneumonic, and septicemic plague in humans. Finegold & Martin, at 230–31.

*Candida albicans* is a yeast-like fungus that causes acute or subacute infection called candidiasis. The yeast may cause lesions in the mouth, esophagus, genitourinary tract, skin, nails, bronchi, lungs and other organs in immunocompromised hosts. Bloodstream infection, endocarditis, and meningitis caused by Candida has been reported. Finegold & Martin, at 429–30.

*Entamoeba histolytica* is a parasitic amoeba that infects the cecum and large bowel of humans, primates, other mammals and birds. *E. histolytica* may penetrate the epithelial tissues of the colon, causing ulceration symptomatic of amoebic dysentery. The amoeba may spread from the colon to the liver via the portal bloodstream and produce abscesses (hepatic amebiasis). In a fraction of these cases, the amoebas may spread to other organs, such as lungs, brain, kidney, skin, and frequently be fatal. *Stedman's Medical Dictionary* 643 (25th ed. 1990). *E. hartmanni* and *E. coli* are more rarely associated with disease in humans. Finegold & Martin, at 497–508.

*Giardia intestinalis* and *G. lambia* parasitize the small intestine of many mammals, including man. Infection with Giardia (giardiasis) may cause diarrhea, abdominal pain, nausea, anorexia, malaise, fatigue, unexplained eosinophilia, dyspepsia and occasionally malabsorption in humans. *Stedman's Medical Dictionary*, at 515; Finegold & Martin, at 497, 508–515.

Poliovirus causes acute viral disease (poliomyelitis) sporadically and in epidemics. The disease is endemic in most warm-weather countries throughout the world. Often waterborne, poliovirus may cause minor illness characterized by fever, sore throat, headache, and vomiting, often accompanied by stiffness of the neck and back.

Importantly, poliovirus may cause major illness involving the central nervous system causing paralysis of one or more limbs. Additionally, one form of poliovirus infection (acute bulbar poliomyelitis) affects the brain stem, motor cortex, and medulla oblongata, causing dysfunction of the swallowing mechanism, and respiratory and circulatory distress. *Dorland's Illustrated Medical Dictionary* 1045 (26th ed. 1981).

This invention provides a method of controlling the above referenced diseases caused by these microorganisms by controlling the growth of these microorganisms in aqueous systems, such as potable water, sewage water, and nonmarine surface water.

An object of this invention is to provide a method for the microbicidal control of unwanted, disease-causing microorganisms in aqueous systems such as potable water, sewage and other nonmarine surface water.

A second object of the invention is to provide methods for controlling microorganisms within the bacterial genera Campylobacter, Shigella, Vibrio and Yersinia, and protozoa within the genera Entamoeba in aqueous systems such as potable water, sewage and other nonmarine surface water.

A third object of this invention relates to providing a method for controlling the growth of the bacteria *Mycobacterium bovis, Salmonella typhi,* and the fungus *Candida albicans* in such aqueous systems.

A fourth object of the invention is to provide a method for controlling poliovirus in aqueous systems such as potable water, sewage, and other nonmarine surface water.

A fifth object is to provide a method for controlling the spread of the diseases caused by the microorganisms discussed above, such as cholera and polio.

Other objects and advantages of the invention will be set forth in the description which follows, and in part will be apparent from the description, or may be learned by practice of the invention.

To achieve the above objects, and in accordance with the purpose of the invention as embodied and broadly described herein, there are provided:

(1) A method for controlling the growth of at least one microorganism in an aqueous system susceptible to the growth of the microorganism and in recognized need of such control comprising the step of adding to the aqueous system an ionene polymer in an amount effective to control the growth of at least one microorganism selected from *Campylobacter spp., Mycobacterium spp., Shigella spp., Vibrio spp., Yersinia spp.,* and *Entamoeba spp.,* and wherein the aqueous system is selected from potable water, sewage, and other nonmarine surface water;

(2) A method for controlling the growth of at least one microorganism in an aqueous system susceptible to the growth of the microorganism and in recognized need of said control comprising the step of adding to the aqueous system an ionene polymer in an amount effective to control the growth of at least one microorganism selected from *Mycobacterium bovis, Salmonella typhi,* and *Candida albicans,* and wherein the aqueous system is selected from potable water, sewage, and other nonmarine surface water;

(3) A method of controlling the spread of cholera transmitted from an aqueous system comprising the step of adding to the aqueous system in recognized need thereof, for the purpose of controlling the spread of cholera, an amount of ionene polymer effective in controlling the growth of *Vibrio spp.,* wherein the aqueous system is selected from potable water, sewage, and other nonmarine surface water; and (4) A method for controlling the spread of polio transmitted from an aqueous system comprising the step of adding to the aqueous system in recognized need thereof, for the purpose of controlling the spread of polio, an amount of ionene polymer effective in controlling the spread of poliovirus, wherein the aqueous system is selected from potable water, sewage, and other nonmarine surface water.

In a first embodiment, the invention relates to a method for controlling the growth of at least one microorganism in an aqueous system susceptible to the growth of the microorganism where the aqueous system is in recognized need of such control. The method comprises the step of adding to the aqueous system an ionene polymer in an amount effective to control the growth at least one microorganism selected from *Campylobacter spp., Mycobacterium spp., Shigella spp., Vibrio spp., Yersinia spp.,* and *Entamoeba spp.* The aqueous system may be selected from potable water, sewage, and other nonmarine surface water.

As discussed above, microorganisms selected from *Campylobacter spp., Mycobacterium spp., Shigella spp., Vibrio spp., Yersinia spp.,* and *Entamoeba spp.* are known to cause diseases in humans as well as other meals by contaminating the water supply. According to this invention, ionene polymers can be effective in controlling the growth of such microorganisms in aqueous systems and, thus, can be effective in controlling the spread of diseases caused by these microorganisms. Specifically, ionene polymers are shown below to be effective in the control of *Campylobacter jejuni, Mycobacterium boris, Shigella dysenteriae, Vibrio cholerae, Vibrio parahaemolyticus, Yersinia enterocolitica,* and the protozoan *Entamoeba histolytica.*

In the methods of this invention, an ionene polymer is used in an amount effective to accomplish the purpose of the particular method, i.e, to control the growth of at least one microoorganism. According to the present invention, control, for example, of the growth or spread of at least one microorganism, means either the inhibition of the growth of a microorganism within the aqueous system or the reduction of the population of a microorganism to an acceptable level. Such control also includes the maintenance of the population of a microorganism in an aqueous system at or below an acceptable level, including zero growth.

The needs of the particular aqueous system determine what amount of ionene polymer will be required to achieve the desired level of control. The concentration of the ionene polymer in a given aqueous system may be, for example, less than or equal to 50 ppm, and preferably less than or equal to 20 ppm. More preferably, the concentration varies from 1 ppm to 10 ppm and most preferably, the ionene polymer is present in the aqueous system at a concentration of approximately 5 ppm.

The methods of the invention are directed to the control of waterborne, disease-causing microorganisms. Thus, the disclosed methods can be employed in any aqueous system which is susceptible to the growth of such microorganisms.

Of particular concern are those aqueous systems that frequently come into contact with humans and other mammals, including livestock, and which can spread the disease-causing microorganism. These aqueous systems include, but are not limited to, potable water, sewage, and other nonmarine surface water such as ponds, lakes, streams, rivers, industrial cooling or contaminant ponds.

A second embodiment of the invention is a method for controlling the growth of at least one microorganism selected from *Mycobacterium bovis, Salmonella typhi,* and *Candida albicans* in an aqueous system susceptible to the growth of the microorganism and in recognized need of that control. The method comprises the step of adding to the aqueous system an ionene polymer in an amount effective to control the growth of at least one of those microorganisms. The aqueous system includes those discussed above and preferably is selected from potable water, sewage, and other nonmarine surface water.

The invention also relates to a method of controlling the spread of cholera transmitted from aqueous systems. This method comprises the step of adding to an aqueous system in recognized need thereof, for the purpose of controlling the spread of cholera, an amount of ionene polymer effective in controlling the growth of Vibrio species. The aqueous system includes those discussed above. Specifically contemplated are those aqueous systems selected from potable water, sewage, and other nonmarine surface water as discussed above.

To control the spread of polio transmitted from an aqueous system, the invention provides a method comprising the step of adding to the aqueous system in recognized need thereof, for the purpose of controlling the spread of polio, an amount of ionene polymer effective in controlling the spread of poliovirus. The aqueous system may be any of those discussed above and preferably is potable water, sewage, or other nonmarine surface water.

Each of the above methods employs at least one ionene polymer to control the growth of the unwanted, disease causing microorganism in an aqueous system. Ionene polymers or polymeric quaternary ammonium compounds, i.e., cationic polymers containing quaternary nitrogens in the polymer backbone (also known as polymeric quats or polyquats), belong to a well-known class of compounds.

Ionene polymers have been reported to possess biological activity. See, e.g., A. Rembaum, *Biological Activity of Ionene Polymers,* Applied Polymer Symposium No. 22, 299–317 (1973).

Ionene polymers have a variety of uses in aqueous systems such as microbicides, bactericides, algicides, sanitizers, and disinfectants. U.S. Pat. Nos. 3,874,870, 3,898,336, 3,931,319, 4,027,020, 4,054,542, 4,089,977, 4,111,679, 4,506,081, 4,581,058, 4,778,813, 4,970,211, 5,051,124, and U.S. Pat. No. 5,093,078, the disclosures of all of which are specifically incorporated by reference herein, give various examples of these polymers and their uses.

Ionene polymers have also been used to inhibit surface adhesion of bacteria and algae, U.S. Pat. No. 5,128,100, the disclosure of which is specifically incorporated by reference herein. However, ionene polymers have heretofore not been known to be useful for controlling the growth of microorganisms such as Campylobacter, Shigella, Vibrio, Yersinia, Entamoeba and poliovirus in aqueous systems. It is thus believed that the uses claimed herein for ionene polymers are novel and are not suggested by any heretofore known uses.

Ionene polymers may be classified according to the repeating unit found in the polymer. This repeating unit results from the reactants used to make the ionene polymer.

A first type of ionene polymer comprises the repeating unit of formula I:

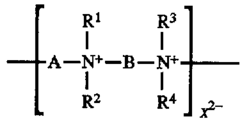

(I)

In this formula, $R^1$, $R^2$, $R^3$, and $R^4$ can be identical or different, and are selected from H, $C_1$–$C_{20}$ alkyl optionally substituted with at least one hydroxyl group, and benzyl optionally substituted on the benzene moiety with at least one $C_1$–$C_{20}$ alkyl group. Preferably, $R^1$, $R^2$, $R^3$ and $R^4$ are all methyl or ethyl.

The group "A" is a divalent radical selected from $C_1$–$C_{10}$ alkyl, $C_2$–$C_{10}$ alkenyl, $C_2$–$C_{10}$ alkynyl, $C_1$–$C_{10}$ hydroxyalkyl, symmetric or asymmetric di-$C_1$–$C_{10}$-alkylether, aryl, aryl-$C_1$–$C_{10}$-alkyl, or $C_1$–$C_{10}$-alkylaryl-$C_1$–$C_{10}$ akyl. Preferably, "A" is $C_1$–$C_5$ alkyl, $C_2$–$C_5$ alkenyl, $C_2$–$C_5$ hydrox-yalkyl, or symmetric di-$C_2$–$C_5$-alkylether, and most preferably "A" is propylene, 2-hydroxypropylene or diethyleneether.

The group "B" is a divalent radical selected from $C_1$–$C_{10}$ alkyl, $C_2$–$C_{10}$ alkenyl, $C_2$–$C_{10}$ alkynyl, $C_1$–$C_{10}$ hydroxyalkyl, aryl, aryl-$C_1$–$C_{10}$-alkyl, or $C_1$–$C_{10}$-alkylaryl-$C_1$–$C_{10}$-alkyl. Preferably, "B" is $C_1$–$C_5$ alkyl, $C_2$–$C_5$ alkenyl, $C_2$–$C_5$ hydroxyalkyl, aryl, aryl-$C_1$–$C_5$-alkyl, or $C_1$–$C_5$ alkylaryl-$C_1$–$C_5$ alkyl. Most preferably "B" is ethylene, propylene, butylene or hexamethylene.

The counter ion, $X^{2-}$, is a divalent counter ion, two monovalent counter ions or a fraction of a polyvalent counter ion sufficient to balance the cationic charge in the repeating unit which forms the ionene polymer backbone. Preferably, $X^{2-}$ is two monovalent anions selected from a halide anion and a trihalide anion and more preferably, chloride or bromide. Ionene polymers having trihalide counter ions are described in U.S. Pat. No. 3,778,476. The disclosure of that patent is incorporated herein by reference.

The ionene polymers having the repeating unit of formula I may be prepared by a number of known methods. One method is to react a diamine of the formula $R^1R^2N$-B-$NR^1R^2$ with a dihalide of the formula X-A-X. Ionene polymers having this repeating unit and methods for their preparation are, for example, described in U.S. Pat. Nos. 3,874,870, 3,931,319, 4,025,627, 4,027,020, 4,506,870 and U.S. Pat. No. 5,093,078; the disclosures of which are incorporated herein by reference. The biological activity of ionene polymers having the repeating unit of formula I is also described in these patents.

A second type of ionene polymer comprises the repeating unit of formula II:

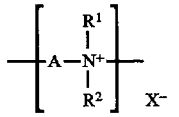

(II)

In this formula II, the definitions of $R^1$, $R^2$, and A are the same as those defined above for formula I. $X^-$ is a monovalent counter ion, one-half of a divalent counter ion or a fraction of a polyvalent counter ion sufficient to balance the cationic charge of the repeating unit which forms the ionene polymer. $X^-$ may be, for example, a halide or trihalide anion and is preferably chloride or bromide.

The ionene polymers having the repeating unit of formula II may be prepared by known methods. One method is to react an amine of the formula $R^1R^2N$ with a haloepoxide such as epichlorohydrin. Ionene polymers having the repeating unit of formula II are, for example, described in U.S. Pat. No. 4,111,679 and U.S. Pat. No. 5,051,124, the disclosures of which are incorporated herein by reference. The biological activity of ionene polymers having the repeating unit of formula II is also described in these patents.

A third type of ionene polymer comprises a repeating unit of formula III:

$$-[R-B']- \quad (III)$$

wherein R is

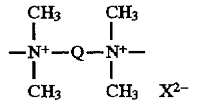

or

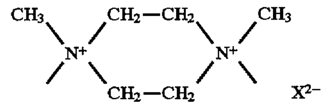

Q is $-(CHR')_p-$, $-CH_2-CH=CH-CH_2-$, $-CH_2-CH_2-O-CH_2-CH_2-$, $-CH_2-CH(OH)-CH_2-$, or

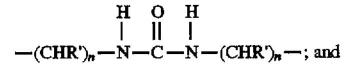

; and

B' is

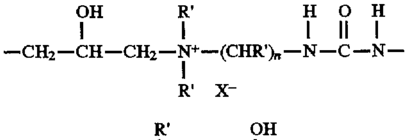

or

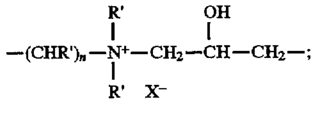

;

wherein: n and p independently vary from 2 to 12; each R' is independently hydrogen or a lower alkyl group; $X^{2-}$ is a divalent counter ion, two monovalent counter ions or a fraction of a polyvalent counter ion sufficient to balance the cationic charge in the group R; and $X^-$ is a monovalent counter ion, one-half of a divalent counter ion or a fraction of a polyvalent counter ion sufficient to balance the cationic charge in the group B'.

Preferably, R' is hydrogen or a $C_1$–$C_4$ alkyl; n is 2–6 and p is 2–6. Most preferably, R' is hydrogen or methyl, n is 3 and p is 2. Preferred counter ions, $X^{2-}$ and $X^-$ are the same as those discussed above in formulae I and II.

The polymers of formula III are derived from bis (dialkylaminoalkyl) ureas, which are also known as urea diamines, by known methods. Ionene polymers of the formula III, methods of their preparation, and their biological activities are, for example, described in U.S. Pat. No. 4,506,081; the disclosure of which is incorporated here by reference.

Ionene polymers comprising the repeating units of formulae I, II, and III may also be cross-linked with primary, secondary or other polyfunctional amines using means known in the art. Ionene polymers can be cross-linked either through the quaternary nitrogen atom or through another functional group attached to the polymer backbone or to a side chain.

Cross-linked ionene polymers, prepared using cross-linking coreactants, are disclosed in U.S. Pat. No. 3,738,945 and Reissue U.S. Pat. No. 28,808, the disclosures of which are incorporated here by reference. The Reissue Patent describes the cross-linking of ionene polymers prepared by the reaction of dimethylamine and epichlorohydrin. The cross-linking coreactants listed are ammonia, primary amines, alkylenediamines, polyglycolamines, piperazines, heteroaromatic diamines and aromatic diamines.

U.S. Pat. No. 5,051,124, the disclosure of which is incorporated herein by reference, describes cross-linked ionene polymers resulting from the reaction of dimethylamine, a polyfunctional amine, and epichlorohydrin. Methods of inhibiting the growth of microorganisms using such cross-linked ionene polymers are also described.

Other examples of various cross-linked ionene polymers and their properties are provided in U.S. Pat. Nos. 3,894,946, 3,894,947, 3,930,877, 4,104,161, 4,164,521, 4,147,627, 4,166,041, 4,606,773, and U.S. Pat. No. 4,769,155. The disclosures of each of these patents is incorporated herein by reference.

The ionene polymers comprising the repeating units of formulae I, II, or III may also be capped, i.e., have a specific end group. Capping may be achieved by means known in the art. For example, an excess of either reactant used to make the ionene polymer can be employed to provide a capping group. Alternatively, a calculated quantity of a monofunctional tertiary amine or monofunctional substituted or unsubstituted alkyl halide can be reacted with an ionene polymer to obtain a capped ionene polymer. Ionene polymers can be capped at one or both ends. Capped ionene polymers and their microbicidal properties are described in U.S. Pat. No. 3,931,319 and U.S. Pat. No. 5,093,078, the disclosures of each of these patents is incorporated herein by reference.

Among the ionene polymers discussed above, a particularly preferred ionene polymer having a repeating unit of formula I is poly[oxyethylene(dimethyliminio)ethylene (dimethyliminio)ethylene dichloride. In this ionene polymer, $R^1$, $R^2$, $R^3$ and $R^4$ are each methyl, A is $-CH_2CH_2OCH_2CH_2-$, B is $-CH_2CH_2-$, and $X^{2-}$ is $2Cl^-$, and the average molecular weight is 1,000–5,000. This ionene polymer is available from Buckman Laboratories, Inc. of Memphis, Tenn. as Busan® 77 product, a 60% aqueous dispersion of the polymer, or WSCP® product, a 60% aqueous dispersion of the polymer. Busan® 77 and WSCP® are biocides used primarily in aqueous systems, including metalworking fluids for microorganism control.

Another particularly preferred ionene polymer having a repeating unit of formula I, also available from Buckman Laboratories, Inc. as Busan® 79 product, or WSCP II product is the ionene polymer where $R^1$, $R^2$, $R^3$ and $R^4$ are each methyl, A is $-CH_2CH(OH)CH_2-$, B is $-CH_2CH_2-$, and $X^{2-}$ is $2Cl^-$. This ionene polymer is a reaction product of N,N,N',N'-tetramethyl-1,2-ethanediamine, with (chloromethyl)-oxirane, and has a 1,000–5,000 average molecular weight. The polymer product Busan® 79 or WSCPII product is a 60% aqueous solution of the polymer.

Preferred ionene polymers having the repeating unit of formula II are those where $R^1$ and $R^2$ are each methyl, A is $—CH_2CH(OH)CH_2—$, and $X^-$ is $Cl^-$. Busan® 1055 product is a 50% aqueous dispersion of such an ionene polymer obtained as a reaction product of dimethylamine with (chloromethyl)oxirane having a 2,000–10,000 average molecular weight.

Busan® 1157 product is a 50% aqueous dispersion of the ionene polymer having the repeating unit of formula II, obtained as a reaction product of dimethylamine with epichlorohydrin, cross-linked with ethylenediamine, where $R^1$ and $R^2$ are each methyl, A is $—CH_2CH(OH)CH_2—$ and $X^-$ is $Cl^-$. This ionene polymer has a 100,000–500,000 average molecular weight.

Busan® 1155 product is a 50% aqueous dispersion of an ionene polymer having the repeating unit of formula II, where $R^1$ and $R^2$ are each methyl, A is $—CH_2CH(OH)CH_2—$, $X^-$ is $Cl^-$ and the ionene polymer is cross-linked with ammonia. This ionene polymer has a molecular weight of approximately 100,000–500,000.

Busan® 1099 product or Bubond® 65 product is a 25% aqueous dispersion of a cross-linked ionene polymer having repeating units of formula II, where $R^1$ and $R^2$ are each methyl, A is $—CH_2CH(OH)CH_2—$, $X^-$ is $Cl^-$, the cross-linking agent is monomethylamine. This ionene polymer has a molecular weight of approximately 10,000–100,000.

Preferred ionene polymers having the repeating unit of formula III are those where R is a urea diamine and B' is $CH_2CH(OH)CH_2$, and $X^-$ is $Cl^-$. BL® 1090 is a 50% aqueous dispersion of the ionene polymer obtained as a reaction product of N,N'-bis-[1—(3—(dimethylamino)-propyl]urea and epichlorohydrin, such an ionene polymer having a 2,000–15,000, preferably 3,000–7,000, average molecular weight.

Each of the above ionene polymers and products identified by trade name is available from Buckman Laboratories, Inc. of Memphis Tenn.

The invention will be demonstrates by the following examples, which are intended merely to be illustrative of the present invention and are not limiting.

EXAMPLE 1

Ionene polymers were evaluated for their effectiveness in killing *Vibrio cholerae* in two levels of water hardness. The following ionene polymer products were used: Busan® 77, Busan® 79, Busan® 1055, Busan® 1099, and Busan® 1157.

The microbicidal activity of each polymer was tested at AOAC water hardness levels of 300 ppm and 900 ppm which measures calcium and magnesium levels. 300 ppm AOAC corresponds to a level of moderately hard water. 900 ppm indicates extremely hard water, approaching brackishness.

For each ionene polymer product, the following weight/weight concentrations of the ionene polymer product in the test system were used: 0.0 ppm, 5.0 ppm, 10.0 ppm, and 20.0 ppm. *V. cholerae* ATCC #14035, GBL #52107, were exposed in aqueous solution supplemented with 0.01% trypticase soy broth for 24 hours at room temperature. Vibriocide survivors were determined by plate count in alkaline trypticase soy agar. The results, which are summarized in Tables 1 through 5, show that ionene polymers, when used in accordance with the present invention, provide dramatic reductions in the viability of *V. cholerae*, as evidence by the decrease in surviving bacteria plated after 24 hours exposure. The complete kill, <10 cfu/ml survivors, at concentrations as low as 5.0 ppm ionene polymer product in AOAC hardness 300 ppm, indicates the effectiveness of ionene polymers against *V. cholerae*. The substantial decrease in the level of surviving *V. cholerae* in as little as 20 ppm in 4 out of 5 of the polymers at AOAC 900 ppm illustrates the effectiveness of ionene polymers against *V. cholerae* even in extremely hard water.

TABLE 1

| | Busan ® 77 | | | |
|---|---|---|---|---|
| Dose Level, ppm | 0 | 5 | 10 | 20 |
| Bacterial Count (cfu/ml) | | | | |
| AOAC 300 ppm | $1.4 \times 10^6$ | <10 | <10 | <10 |
| AOAC 900 ppm | $1.2 \times 10^7$ | $1.2 \times 10^3$ | $9.1 \times 10^2$ | $4.7 \times 10^2$ |

TABLE 2

| | Busan ® 79 | | | |
|---|---|---|---|---|
| Dose Level, ppm | 0 | 5 | 10 | 20 |
| Bacterial Count (cfu/ml) | | | | |
| AOAC 300 ppm | $1.4 \times 10^6$ | <10 | <10 | <10 |
| AOAC 900 ppm | $1.2 \times 10^7$ | $2.1 \times 10^5$ | $2.3 \times 10^3$ | 70 |

TABLE 3

| | Busan ® 1055 | | | |
|---|---|---|---|---|
| Dose Level, ppm | 0 | 5 | 10 | 20 |
| Bacterial Count (cfu/ml) | | | | |
| AOAC 300 ppm | $1.4 \times 10^6$ | <10 | <10 | <10 |
| AOAC 900 ppm | $1.2 \times 10^7$ | $2.0 \times 10^6$ | $1.3 \times 10^5$ | $9.1 \times 10^3$ |

TABLE 4

| | Busan ® 1099 | | | |
|---|---|---|---|---|
| Dose Level, ppm | 0 | 5 | 10 | 20 |
| Bacterial Count (cfu/ml) | | | | |
| AOAC 300 ppm | $1.4 \times 10^6$ | <10 | <10 | <10 |
| AOAC 900 ppm | $1.2 \times 10^7$ | $6.2 \times 10^5$ | $4.0 \times 10^5$ | $2.5 \times 10^4$ |

TABLE 5

| | Busan ® 1157 | | | |
|---|---|---|---|---|
| Dose Level, ppm | 0 | 5 | 10 | 20 |
| Bacterial Count (cfu/ml) | | | | |
| AOAC 300 ppm | $1.4 \times 10^6$ | <10 | <10 | <10 |
| AOAC 900 ppm | $1.2 \times 10^7$ | $1.2 \times 10^7$ | $1.5 \times 10^6$ | $3.7 \times 10^6$ |

EXAMPLE 2

Ionene polymer products Bubond® 65, Busan® 77, Busan® 79 and Busan® 1055 were evaluated for effectiveness in killing the bacteria *Campylobacter jejuni, Escherichia coli, Mycobacterium boris, Pseudomonas aeruginosa, Salmonella typhi, Shigella dysenteriae, Staphylococcus aureus, Vibrio parahaemolyticus* ATCC 17802, *Yersinia enterocolitica,* and the yeast *Candida albicans,* in deionized water and artificial pond water. Results are shown in Tables 6–9.

Sterile deionized water, pH 7 to 7.5, was supplemented with polymer products at the concentrations of 2.5 ppm, 10 ppm, and 20 ppm.

Artificial pond water consisted of sterile deionized water, sterile salts (350 ppm KCl, 350 ppm $CaCl_2$, 350 ppm NaCl) and 0.01% sterile trypticase soy broth. Polymer products were added to this medium at concentrations of 5 ppm, 10 ppm, and 20 ppm.

Bacteria, except for *Campylobacter jejuni* and *Mycobacterium Bovis*, and yeast were cultured in trypticase soy broth for 24–36 hours and seeded into 100 ml of the test solution at a concentration of $10^4$cfu/ml. The bacteria and yeast were contacted with the solution for 18–24 hours at 20°–25° C. without agitation, then quantitated by standard pour plate methodology in trypticase soy agar.

*Campylobacter jejuni* growth was quantitated by spread plate technique on Chocolate Agar, and incubated at 37° C. in a BBL "Campy Pack" for 48 hours. *Mycobacterium bovis* growth was quantitated by membrane filtration and cultivated in Glucose Base broth at 35° C. for 28 days.

TABLE 6

Microbicidal Activity of Bubond ® 65

| Dose Level, ppm | 0 | 2.5 | 5 | 10 | 20 |
|---|---|---|---|---|---|
| Bacterial Count (cfu/ml) | | | | | |
| *Campylobacter jejuni* | | | | | |
| Deionized Water | $1.0 \times 10^4$ | <10 | NT | <10 | <10 |
| Artificial Pond Water | $1.0 \times 10^4$ | NT | <10 | <10 | <10 |
| *Escherichia coli* | | | | | |
| Deionized Water | $1.0 \times 10^4$ | $5.0 \times 10^3$ | NT | <10 | <10 |
| Artificial Pond Water | $1.0 \times 10^5$ | NT | $3.0 \times 10^4$ | <10 | <10 |
| *Pseudomonas aeruginosa* | | | | | |
| Deionized Water | $1.0 \times 10^4$ | <10 | NT | <10 | <10 |
| Artificial Pond Water | $1.0 \times 10^5$ | NT | 210 | <10 | <10 |
| *Salmonella typhi* | | | | | |
| Deionized Water | $1.0 \times 10^4$ | $3.1 \times 10^4$ | NT | <10 | <10 |
| Artificial Pond Water | $1.0 \times 10^5$ | NT | $1.6 \times 10^4$ | <10 | <10 |
| *Shigella dysenteriae* | | | | | |
| Deionized Water | $1.0 \times 10^4$ | <10 | NT | <10 | <10 |
| Artificial Pond Water | $1.0 \times 10^4$ | NT | <10 | <10 | <10 |
| *Staphylococcus aureus* | | | | | |
| Deionized Water | $1.0 \times 10^6$ | <10 | NT | <10 | <10 |
| Artificial Pond Water | $1.0 \times 10^4$ | NT | <10 | <10 | <10 |
| *Vibrio parahaemolyticus* | | | | | |
| Deionized Water | $1.0 \times 10^6$ | <10 | NT | <10 | <10 |
| Artificial Pond Water | $1.0 \times 10^5$ | NT | 600 | 470 | 750 |
| *Yersinia enterocolitica* | | | | | |
| Deionized Water | $1.0 \times 10^4$ | <10 | NT | <10 | <10 |
| Artificial Pond Water | $1.0 \times 10^4$ | NT | <10 | <10 | <10 |
| *Mycobacterium bovis* | | | | | |
| Deionized Water | 28 | <1 | NT | NT | NT |

TABLE 6-continued

Microbicidal Activity of Bubond ® 65

| Dose Level, ppm | 0 | 2.5 | 5 | 10 | 20 |
|---|---|---|---|---|---|
| Artificial Pond Water | 28 | NT | 9 | NT | NT |
| Yeast Count | | | | | |
| *Candida albicans* | | | | | |
| Deionized Water | $1.0 \times 10^4$ | <10 | NT | <10 | <10 |
| Artificial Pond Water | $1.0 \times 10^4$ | NT | <10 | <10 | <10 |

NT = Not tested

TABLE 7

Microbicidal Activity of Busan ® 77

| Dose Level, ppm | 0 | 2.5 | 5 | 10 | 20 |
|---|---|---|---|---|---|
| Bacterial Count (cfu/ml) | | | | | |
| *Campylobacter jejuni* | | | | | |
| Deionized Water | $1.0 \times 10^4$ | <10 | NT | <10 | <10 |
| Artificial Pond Water | $1.0 \times 10^4$ | NT | <10 | <10 | <10 |
| *Escherichia coli* | | | | | |
| Deionized Water | $1.0 \times 10^4$ | <10 | NT | <10 | <10 |
| Artificial Pond Water | $1.0 \times 10^5$ | NT | <10 | <10 | <10 |
| *Pseudomonas aeruginosa* | | | | | |
| Deionized Water | $1.0 \times 10^4$ | <10 | NT | <10 | <10 |
| Artificial Pond Water | $1.0 \times 10^5$ | NT | 810 | <10 | <10 |
| *Salmonella typhi* | | | | | |
| Deionized Water | $1.0 \times 10^4$ | 50 | NT | <10 | <10 |
| Artificial Pond Water | $1.0 \times 10^5$ | NT | 620 | <10 | <10 |
| *Shigella dysenteriae* | | | | | |
| Deionized Water | $1.0 \times 10^4$ | <10 | NT | <10 | <10 |
| Artificial Pond Water | $1.0 \times 10^4$ | NT | <10 | <10 | <10 |
| *Staphylococcus aureus* | | | | | |
| Deionized Water | $1.0 \times 10^6$ | <10 | NT | <10 | <10 |
| Artificial Pond Water | $1.0 \times 10^4$ | NT | <10 | <10 | <10 |
| *Vibrio parahaemolyticus* | | | | | |
| Deionized Water | $1.0 \times 10^6$ | 700 | NT | <10 | <10 |
| Artificial Pond Water | $1.0 \times 10^5$ | NT | $2.1 \times 10^3$ | 570 | <10 |
| *Yersinia enterocolitica* | | | | | |
| Deionized Water | $1.0 \times 10^4$ | <10 | NT | <10 | <10 |
| Artificial Pond Water | $1.0 \times 10^4$ | NT | <10 | <10 | <10 |
| *Mycobacterium bovis* | | | | | |
| Deionized Water | 28 | <1 | NT | NT | NT |
| Artificial Pond Water | 28 | NT | 9 | NT | NT |
| Yeast Count | | | | | |
| *Candida albicans* | | | | | |
| Deionized Water | $1.0 \times 10^4$ | <10 | NT | <10 | <10 |
| Artificial Pond Water | $1.0 \times 10^4$ | NT | 40 | <10 | <10 |

NT = Not tested

TABLE 8

Microbicidal Activity of Busan® 79

| Dose Level, ppm | 0 | 2.5 | 5 | 10 | 20 |
|---|---|---|---|---|---|
| Bacterial Count (cfu/ml) | | | | | |
| *Campylobacter jejuni* | | | | | |
| Deionized Water | 1.0 × $10^4$ | <10 | NT | <10 | <10 |
| Artificial Pond Water | 1.0 × $10^4$ | NT | <10 | <10 | <10 |
| *Escherichia coli* | | | | | |
| Deionized Water | 1.0 × $10^4$ | 2.1 × $10^4$ | NT | <10 | <10 |
| Artificial Pond Water | 1.0 × $10^5$ | NT | <10 | <10 | <10 |
| *Pseudomonas aeruginosa* | | | | | |
| Deionized Water | 1.0 × $10^4$ | <10 | NT | <10 | <10 |
| Artificial Pond Water | 1.0 × $10^5$ | NT | <10 | <10 | <10 |
| *Salmonella typhi* | | | | | |
| Deionized Water | 1.0 × $10^4$ | <10 | NT | <10 | <10 |
| Artificial Pond Water | 1.0 × $10^5$ | NT | <10 | <10 | <10 |
| *Shigella dysenteriae* | | | | | |
| Deionized Water | 1.0 × $10^4$ | <10 | NT | <10 | <10 |
| Artificial Pond Water | 1.0 × $10^4$ | NT | <10 | <10 | <10 |
| *Staphylococcus aureus* | | | | | |
| Deionized Water | 1.0 × $10^6$ | <10 | NT | <10 | <10 |
| Artificial Pond Water | 1.0 × $10^4$ | NT | <10 | <10 | <10 |
| *Vibrio parahaemolyticus* | | | | | |
| Deionized Water | 1.0 × $10^6$ | <10 | NT | <10 | <10 |
| Artificial Pond Water | 1.0 × $10^5$ | NT | 1.05 × $10^3$ | 450 | <10 |
| *Yersinia enterocolitica* | | | | | |
| Deionized Water | 1.0 × $10^4$ | <10 | NT | <10 | <10 |
| Artificial Pond Water | 1.0 × $10^4$ | NT | <10 | <10 | <10 |
| *Mycobacterium bovis* | | | | | |
| Deionized Water | 28 | 5 | NT | NT | NT |
| Artificial Pond Water | 28 | NT | 1 | NT | NT |
| Yeast Count | | | | | |
| *Candida albicans* | | | | | |
| Deionized Water | 1.0 × $10^4$ | <10 | NT | <10 | <10 |
| Artificial Pond Water | 1.0 × $10^4$ | NT | <10 | <10 | <10 |

NT = Not tested

TABLE 9

Microbicidal Activity of Busan® 1055

| Dose Level, ppm | 0 | 2.5 | 5 | 10 | 20 |
|---|---|---|---|---|---|
| Bacterial Count (cfu/ml) | | | | | |
| *Campylobacter jejuni* | | | | | |
| Deionized Water | 1.0 × $10^4$ | <10 | NT | <10 | <10 |
| Artificial Pond Water | 1.0 × $10^4$ | NT | <10 | <10 | <10 |
| *Escherichia coli* | | | | | |
| Deionized Water | 1.0 × $10^4$ | <10 | NT | <10 | <10 |
| Artificial Pond Water | 1.0 × $10^5$ | NT | <10 | <10 | <10 |
| *Pseudomonas aeruginosa* | | | | | |
| Deionized Water | 1.0 × $10^4$ | <10 | NT | <10 | <10 |
| Artificial Pond Water | 1.0 × $10^5$ | NT | <10 | <10 | <10 |
| *Salmonella typhi* | | | | | |

TABLE 9-continued

Microbicidal Activity of Busan® 1055

| Dose Level, ppm | 0 | 2.5 | 5 | 10 | 20 |
|---|---|---|---|---|---|
| Deionized Water | 1.0 × $10^4$ | <10 | NT | <10 | <10 |
| Artificial Pond Water | 1.0 × $10^5$ | NT | <10 | <10 | <10 |
| *Shigella dysenteriae* | | | | | |
| Deionized Water | 1.0 × $10^4$ | <10 | NT | <10 | <10 |
| Artificial Pond Water | 1.0 × $10^4$ | NT | <10 | <10 | <10 |
| *Staphylococcus aureus* | | | | | |
| Deionized Water | 1.0 × $10^6$ | 2.9 × $10^4$ | NT | <10 | <10 |
| Artificial Pond Water | 1.0 × $10^4$ | NT | <10 | <10 | <10 |
| *Vibrio parahaemolyticus* | | | | | |
| Deionized Water | 1.0 × $10^6$ | <10 | NT | <10 | <10 |
| Artificial Pond Water | 1.0 × $10^5$ | NT | 3.1 × $10^2$ | <10 | <10 |
| *Yersinia enterocolitica* | | | | | |
| Deionized Water | 1.0 × $10^4$ | <10 | NT | <10 | <10 |
| Artificial Pond Water | 1.0 × $10^4$ | NT | <10 | <10 | <10 |
| *Mycobacterium bovis* | | | | | |
| Deionized Water | 28 | NT | NT | NT | <.001 |
| Artificial Pond Water | 28 | NT | NT | <.001 | NT |
| Yeast Count | | | | | |
| *Candida albicans* | | | | | |
| Deionized Water | 1.0 × $10^4$ | <10 | NT | <10 | <10 |
| Artificial Pond Water | 1.0 × $10^4$ | NT | <10 | <10 | <10 |

NT = Not tested

EXAMPLE 3

Ionene polymer products Bubond® 65, Busan® 77, Busan® 79 and Busan® 1055 were evaluated for effectiveness in killing the protozoan *Entamoeba histolytica* ATCC 30922 GBL Lab. No. 42409.

Effectiveness of these polymer products was tested in deionized water and artificial pond water as described in Example 2. The concentration of Entamoeba trophozoites in the inoculum was 320/ml. Entamoeba were enumerated, as shown in Tables 10–13, by direct microscopic observation of motility in a hemocytometer counting chamber at 400x.

TABLE 10

Microbicidal Activity of Bubond® 65

| Dose Level, ppm | 0 | 2.5 | 5 | 10 | 20 |
|---|---|---|---|---|---|
| Number of Motile Organisms/ml *Entamoeba histolytica* | | | | | |
| Deionized Water | 768 | <1 | NT | <1 | <1 |
| Artificial Pond Water | 1086 | NT | <1 | <1 | <1 |

TABLE 11

Microbicidal Activity of Busan® 77

| Dose Level, ppm | 0 | 2.5 | 5 | 10 | 20 |
|---|---|---|---|---|---|
| Number of Motile Organisms/ml *Entamoeba histolytica* | | | | | |
| Deionized Water | 768 | <1 | NT | <1 | <1 |
| Artificial Pond Water | 1086 | NT | <1 | <1 | <1 |

TABLE 12

Microbicidal Activity of Busan ® 79

| Dose Level, ppm | 0 | 2.5 | 5 | 10 | 20 |
|---|---|---|---|---|---|
| Number of Motile Organisms/ml *Entamoeba histolytica* | | | | | |
| Deionized Water | 768 | <1 | NT | <1 | <1 |
| Artificial Pond Water | 1086 | NT | <1 | <1 | <1 |

TABLE 13

Microbicidal Activity of Busan ® 1055

| Dose Level, ppm | 0 | 2.5 | 5 | 10 | 20 |
|---|---|---|---|---|---|
| Number of Motile Organisms/ml *Entamoeba histolytica* | | | | | |
| Deionized Water | 768 | <1 | NT | <1 | <1 |
| Artificial Pond Water | 1086 | NT | <1 | <1 | <1 |

The concentration (ppm of the ionene polymer product in the test system) of Bubond® 65, Busan® 77, Busan® 79 and Busan® 1055 required to kill at least 99.9% of the tested pathogenic microorganisms is summarized in Tables 14–17.

TABLE 14

Microbicidal Activity of Bubond ® 65

| | Concentrations (ppm) | |
|---|---|---|
| Microorganism | Deionized Water | Artificial Pond Water |
| Bacteria: | | |
| *Campylobacter jejuni* | 2.5 | 5 |
| *Escherichia coli* | 10 | 10 |
| *Mycobacterium bovis* | 2.5 | 5 |
| *Pseudomonas aeruginosa* | 2.5 | 5 |
| *Salmonella typhi* | 10 | 10 |
| *Shigella dysenteriae* | 2.5 | 5 |
| *Staphylococcus aureus* | 2.5 | 5 |
| *Vibrio parahaemolyticus* | 2.5 | 5 |
| *Yersinia enterocolitica* | 2.5 | 5 |
| Yeast: | | |
| *Candida albicans* | 2.5 | 5 |
| Protozoa (trophozoites): | | |
| *Entamoeba histolytica* | 2.5 | 5 |

TABLE 15

Microbicidal Activity of Busan ® 77

| | Concentrations (ppm) | |
|---|---|---|
| Microorganism | Deionized Water | Artificial Pond Water |
| Bacteria: | | |
| *Campylobacter jejuni* | 2.5 | 5 |
| *Escherichia coli* | 2.5 | 5 |
| *Mycobacterium bovis* | 2.5 | 5 |
| *Pseudomonas aeruginosa* | 2.5 | 5 |
| *Salmonella typhi* | 2.5 | 5 |
| *Shigella dysenteriae* | 2.5 | 5 |
| *Staphylococcus aureus* | 2.5 | 5 |
| *Vibrio parahaemolyticus* | 2.5 | 10 |
| *Yersinia enterocolitica* | 2.5 | 5 |
| Yeast: | | |
| *Candida albicans* | 2.5 | 5 |

TABLE 15-continued

Microbicidal Activity of Busan ® 77

| | Concentrations (ppm) | |
|---|---|---|
| Microorganism | Deionized Water | Artificial Pond Water |
| Protozoa (trophozoites): | | |
| *Entamoeba histolytica* | 2.5 | 5 |

TABLE 16

Microbicidal Activity of Busan ® 79

| | Concentrations (ppm) | |
|---|---|---|
| Microorganism | Deionized Water | Artificial Pond Water |
| Bacteria: | | |
| *Campylobacter jejuni* | 2.5 | 5 |
| *Escherichia coli* | 10 | 5 |
| *Mycobacterium bovis* | 10 | 5 |
| *Pseudomonas aeruginosa* | 2.5 | 5 |
| *Salmonella typhi* | 2.5 | 5 |
| *Shigella dysenteriae* | 2.5 | 5 |
| *Staphylococcus aureus* | 2.5 | 5 |
| *Vibrio parahaemolyticus* | 2.5 | 10 |
| *Yersinia enterocolitica* | 2.5 | 5 |
| Yeast: | | |
| *Candida albicans* | 2.5 | 5 |
| Protozoa (trophozoites): | | |
| *Entamoeba histolytica* | 2.5 | 5 |

TABLE 17

Microbicidal Activity of Busan ® 1055

| | Concentrations (ppm) | |
|---|---|---|
| Microorganism | Deionized Water | Artificial Pond Water |
| Bacteria: | | |
| *Campylobacter jejuni* | 2.5 | 5 |
| *Escherichia coli* | 2.5 | 5 |
| *Mycobacterium bovis* | 2.5 | 5 |
| *Pseudomonas aeruginosa* | 2.5 | 5 |
| *Salmonella typhi* | 2.5 | 5 |
| *Shigella dysenteriae* | 2.5 | 5 |
| *Staphylococcus aureus* | 10 | 5 |
| *Vibrio parahaemolyticus* | 2.5 | 10 |
| *Yersinia enterocolitica* | 2.5 | 5 |
| Yeast: | | |
| *Candida albicans* | 2.5 | 5 |
| Protozoa (trophozoites): | | |
| *Entamoeba histolytica* | 2.5 | 5 |

EXAMPLE 4

Ionene polymer products Bubond® 65, Busan® 77, Busan® 79 and Busan® 1055, were evaluated for effectiveness against poliovirus. 0.3 ml of poliovirus Type 1, maintained as a stock solution (of greater than or equal to $10^6$ TC $ID_{50}$) in EMEM containing 5% calf serumwas added to 100 ml of the test solutions described in Example 2. Virus viability was quantitated by calculation of the TC $ID_{50}$, (the average of one Tissue Culture Infectious Dose for 50% of the test units.) The virus (0.1 ml per well) was cultivated in Hep-2 cells for 5 days at 37° C., 8–10% $CO_2$. Virus growth, as shown in Tables 18–21, was established by microscopic observation of cytopathic effect to the cell monolayer.

TABLE 18

| Microbicidal Activity of Bubond ® 65 Against Poliovirus | | | | | |
|---|---|---|---|---|---|
| Dose Level, ppm | 0 | 2.5 | 5 | 10 | 20 |
| TC $ID_{50}$ | | | | | |
| Deionized Water | $10^{5.5}$ | $10^{4.7}$ | NT | $10^{4.5}$ | $10^{5.3}$ |
| Artificial Pond Water | $10^{4.0}$ | NT | $10^{4.3}$ | $10^{4.5}$ | $10^{4.0}$ |

TABLE 19

| Microbicidal Activity of Busan ® 77 Against Poliovirus | | | | | |
|---|---|---|---|---|---|
| Dose Level, ppm | 0 | 2.5 | 5 | 10 | 20 |
| TC $ID_{50}$ | | | | | |
| Deionized Water | $10^{5.5}$ | $10^{3.7}$ | NT | $10^{4.7}$ | $10^{5.3}$ |
| Artificial Pond Water | $10^{4.0}$ | NT | $10^{3.7}$ | $10^{4.5}$ | $10^{4.0}$ |

TABLE 20

| Microbicidal Activity of Busan ® 79 Against Poliovirus | | | | | |
|---|---|---|---|---|---|
| Dose Level, ppm | 0 | 2.5 | 5 | 10 | 20 |
| TC $ID_{50}$ | | | | | |
| Deionized Water | $10^{5.5}$ | $10^{4.5}$ | NT | $10^{4.5}$ | $10^{4.3}$ |
| Artificial Pond Water | $10^{4.0}$ | NT | $10^{4.0}$ | $10^{4.3}$ | $10^{4.3}$ |

TABLE 21

| Microbicidal Activity of Busan ® 1055 Against Poliovirus | | | | | |
|---|---|---|---|---|---|
| Dose Level, ppm | 0 | 2.5 | 5 | 10 | 20 |
| TC $ID_{50}$ | | | | | |
| Deionized Water | $10^{5.5}$ | $10^{5.3}$ | NT | $10^{3.7}$ | $10^{4.7}$ |
| Artificial Pond Water | $10^{4.0}$ | NT | $10^{5.7}$ | $10^{4.7}$ | $10^{3.7}$ |

The invention claimed is:

1. A method for controlling the growth of at least one microorganism selected from Vibfio spp. in an aqueous system susceptible to the growth of said microorganism and in recognized need of said control comprising the step of adding to said aqueous system an ionene polymer in an amount effective to control the growth of said at least one microorganism, wherein said aqueous system is selected from potable water, sewage, and other nonmarine surface water, and said ionene polymer comprises a repeating unit of the formula (I):

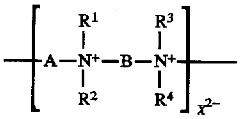

(I)

wherein:

$R^1$, $R^2$, $R^3$, and $R^4$ are each methyl;

A is $—CH_2CH_2OCH_2CH_2—$ or $—CH_2CH(OH)CH_2—$;

B is $—CH_2CH_2—$; and $X^{2-}$ is $2Cl^-$; and wherein the molecular weight of said ionene polymer ranges from 1,000 to 5,000.

2. The method of claim 1, wherein said Vibrio bacteria is *Vibrio cholerae.*

3. The method of claim 1, wherein said Vibrio bacteria is *Vibrio parahaemolyticus.*

4. The method of claim 1, wherein the concentration of said ionene polymer in said potable water is 5 ppm.

5. A method for controlling the growth of at least one microorganism selected from Vibrio spp. in an aqueous system susceptible to the growth of said microorganism and in recognized need of said control comprising the step of adding to said aqueous system an ionene polymer in an amount effective to control the growth of said at least one microorganism, wherein said aqueous system is selected from potable water, sewage, and other nonmarine surface water, and said ionene polymer comprises a repeating unit of the formula (II):

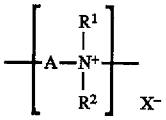

(II)

wherein:

$R^1$ and $R^2$ are each methyl;

A is $—CH_2CH(OH)CH_2—$; and $X^-$ is $Cl^-$; and wherein the molecular weight of said ionene polymer ranges from 2,000 to 500,000.

6. A method for controlling the spread of cholera transmitted from an aqueous system comprising the step of adding to said aqueous system in recognized need thereof, for the purpose of controlling the spread of cholera, an amount of ionene polymer effective in controlling the growth of at least one microorganism selected from Vibrio spp., wherein said aqueous system is selected from potable water, sewage, and other nonmarine surface water, and said ionene polymer comprises a repeating unit of the formula (I):

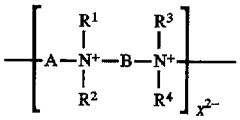

(I)

wherein:

$R^1$, $R^2$, $R^3$, and $R^4$ are each methyl;

A is $—CH_2CH_2OCH_2CH_2—$ or $—CH_2CH(OH)CH_2—$;

B is $—CH_2CH_2—$; and $X^{2-}$ is $2Cl^-$; and wherein the molecular weight of said ionene polymer ranges from 1,000 to 5,000.

7. A method for controlling the spread of cholera transmitted from an aqueous system comprising the step of adding to said aqueous system in recognized need thereof, for the purpose of controlling the spread of cholera, an amount of ionene polymer effective in controlling the growth of at least one microorganism selected from Vibrio spp., wherein said aqueous system is selected from potable water, sewage, and other nonmarine surface water, and said ionene polymer comprises a repeating unit of the formula (II):

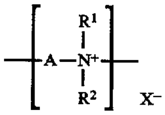

(II)

wherein:

$R^1$ and $R^2$ are each methyl;

A is $—CH_2CH(OH)CH_2—$; and $X^-$ is $Cl^-$; and wherein the molecular weight of said ionene polymer ranges from 2,000 to 500,000.

* * * * *

UNITED STATES PATENT AND TRADEMARK OFFICE

CERTIFICATE OF CORRECTION

PATENT NO.: 5,681,862
DATED : October 28, 1997
INVENTOR(S): C. George Hollis et al.

It is certified that error appears in the above-identified patent and that said Letters Patent is hereby corrected as shown below:

Title page, item [57],
In the Abstract, line 7, "*ribrio*" should read --*Vibrio*--

In column 17, line 45, claim 1, "Vibfio" should read --Vibrio--.

Signed and Sealed this

Tenth Day of February, 1998

Attest:

BRUCE LEHMAN

*Attesting Officer* *Commissioner of Patents and Trademarks*